(12) United States Patent
Reu et al.

(10) Patent No.: US 9,359,342 B2
(45) Date of Patent: Jun. 7, 2016

(54) PROTEIN DISULFIDE ISOMERASE INHIBITING ANTICANCER AGENTS

(71) Applicant: THE CLEVELAND CLINIC FOUNDATION, Cleveland, OH (US)

(72) Inventors: Frederic J. Reu, Beachwood, OH (US); Jim Phillips, Bay Village, OH (US); Sergei Vatolin, Bay Village, OH (US); Dale Grabowski, Parma, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/536,911

(22) Filed: Nov. 10, 2014

(65) Prior Publication Data

US 2015/0133514 A1    May 14, 2015

Related U.S. Application Data

(60) Provisional application No. 61/901,777, filed on Nov. 8, 2013, provisional application No. 62/008,551, filed on Jun. 6, 2014.

(51) Int. Cl.
  *C07D 417/06* (2006.01)
  *C07D 417/14* (2006.01)
  *C07D 495/04* (2006.01)
  *A61K 47/48* (2006.01)

(52) U.S. Cl.
  CPC ........ *C07D 417/06* (2013.01); *A61K 47/48061* (2013.01); *A61K 47/48215* (2013.01); *C07D 417/14* (2013.01); *C07D 495/04* (2013.01)

(58) Field of Classification Search
  CPC ... C07D 417/06; C07D 417/14; C07D 495/04
  See application file for complete search history.

(56) References Cited

U.S. PATENT DOCUMENTS

2006/0276520 A1   12/2006   Singh et al.

FOREIGN PATENT DOCUMENTS

WO            0032598 A1      6/2000

OTHER PUBLICATIONS

National Center for Biotechnology Information, PubChem Compound Database; CID=2175930, https://pubchem.ncbi.nlm.nih.gov/compound/2175930 (accessed Sep. 30, 2015), which has a create date of Jul. 14, 2005.*
National Center for Biotechnology Information. PubChem Compound Database; CID=1820763, https://pubchem.ncbi.nlm.nih.gov/compound/1820763 (accessed Sep. 30, 2015), which has a create date of Jul. 12, 2005.*
Xu et al. Drug Discovery Today, 2014, 19, 222-240.*
American Cancer Society, Multiple Myeloma, Can multiple myeloma be prevented? obtained from http://www.cancer.org/cancer/multiplemyeloma/detailedguide/multiple-myeloma-prevention on Sep. 29, 2015.*
WebMD, Leukemia, Lymphoma / Blood Cancers Mini Guide TOC—Prevention, obtained from http://www.webmd.com/cancer/lymphoma/non-hodgkins-lymphoma-prevention on Sep. 29, 2015.*
Avet-Loiseau et al., "Bortezomib Plus Dexamethasone Induction Improves Outcome of Patients with t(4;14) Myeloma but Not Outcome of Patients with del(17p)", Journal of Clinical Oncology, vol. 28, No. 30, Oct. 20, 2010, pp. 4630-4634.
Bose et al., "Bortexomib for the Treatment of Non-Hodgkin's Lymphoma", Expert Opinion Pharmacother, 2014, 15(16), pp. 1-17.
Kronke et al., "Lenalidomide Causes Selective Degradation of IKZF1 and IKZF3 in Multiple Myeloma Cells", Science, Jan. 2014, 17; 343(6168), pp. 1-11.
Lavoie et al., "Dimerization-Induced Allostery in Protein Kinase Regulation", Trends in Biochemical Science, Oct. 2014, vol. 39, No. 10, pp. 475-486.
Lee et al., "Thioredoxin-Interacting Protein Regulates Protein Disulfide Isomerases and Endoplasmic Reticulum Stress", EMBO Molecular Medicine, vol. 6, No. 6, 2014, pp. 732-743.
Neben et al., "Administration of Bortezomib Before and After Autologous Stem Cell Transplantation Improves Outcome in Multiple Myeloma Patients with Deletion 17p", Blood, Jan. 26, 2012, vol. 119, No. 4, pp. 940-948.
Richardson et al., "A Phase 2 Study of Bortezomib in Relapsed, Refractory Myeloma", The New England Journal of Medicine, 348:26, Jun. 26, 2003, pp. 2609-2617.
Xu et al., "Protein Disulfide Isomerase: A Promising Target for Cancer Therapy", Drug Discovery Today, vol. 00, No. 00, Nov. 2013, pp. 1-19.
Zhang et al., "Development of Inhibitors in the Ubiquitination Cascade", FEBS Letters, 588 (2014) 356-367.
Beharry et al., "Novel Benzylidene-Thiazolidine-2,4-Diones Inhibit Pim Protein Kinase Activity and Induce Cell Cycle Arrest in Leukemia and Prostate Cancer Cells", Mol Cancer Ther., Jun. 2009, 8(6), pp. 1-18.
PCT International Search Report and Written Opinion for PCT/US14/64745, mailed Jan. 12, 2015, pp. 1-8.

* cited by examiner

*Primary Examiner* — Matthew Coughlin
(74) *Attorney, Agent, or Firm* — Tarolli, Sundheim, Covell & Tummino LLP

(57) ABSTRACT

Protein disulfide isomerase inhibitors according to formula I

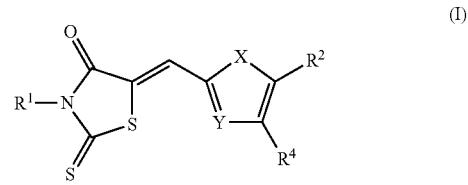

are described, wherein $R^1$ is an aryl or cycloalkyl group, $R^2$ is selected from the group consisting of CN, $SO_2CH_3$, $NO_2$, $CO_2R^3$, $CONHR^3$, $NMe_2$, and $CF_3$, $R^3$ is selected from H or lower alkyl, $R^4$ is H, halogen, CN, or COOH, and X and Y are C—H or heteroatoms selected from the group consisting of N, O, and S. The protein disulfide isomerase inhibitors can be used for the treatment of cancer in a subject.

14 Claims, 6 Drawing Sheets

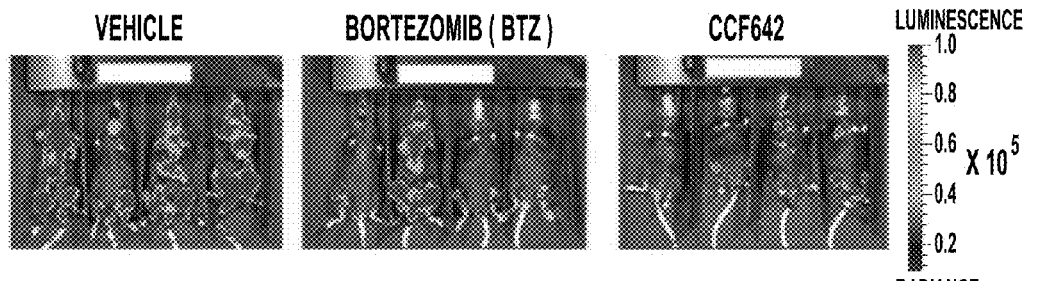
FIG. 3A
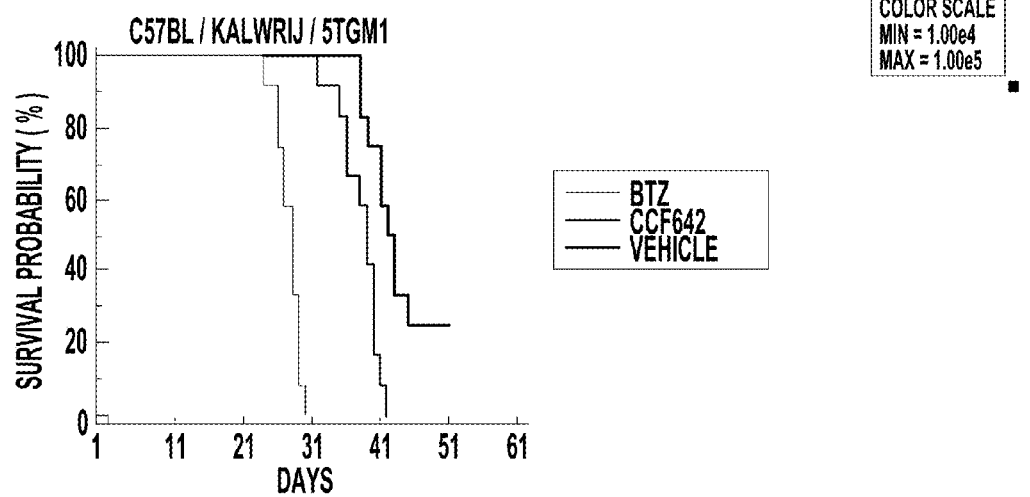
FIG. 3B
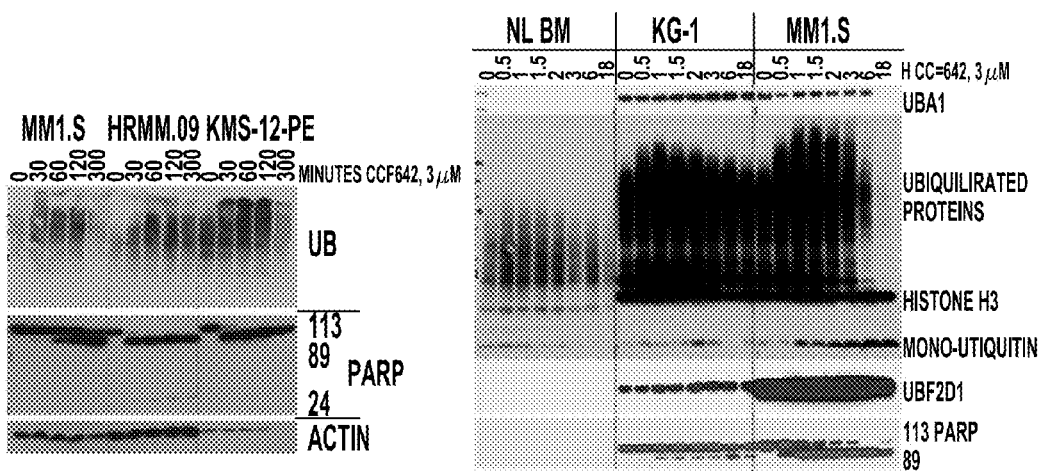
FIG. 4A
FIG. 4B

PROTEIN DISULFIDE ISOMERASE INHIBITING ANTICANCER AGENTS

CROSS-REFERENCE TO RELATED APPLICATIONS

This application claims priority from U.S. Provisional Application Ser. No. 61/901,777, filed Nov. 8, 2013, and U.S. Provisional Application Ser. No. 62/008,551, filed Jun. 6, 2014, the entire contents of which are incorporated herein by reference.

BACKGROUND

The ubiquitin proteasome system (UPS) consists of a cascade of enzymatic steps that are initiated by E1 ubiquitin activating enzyme which after loading two ubiquitin molecules transfers one to E2 conjugating enzymes that in concert with a large number (~1000) of protein specificity conferring E3 ligases attach ubiquitin chains to target proteins. Finley et al., Cell, 116(2 Suppl):S29-32, 22 p following S32 (2004). Depending on how ubiquitin is attached this can either alter cellular localization and function or target the protein for degradation in the proteasome. Deubiquitinases counter-regulate by removing ubiquitin tags.

Studies in multiple myeloma (MM) have established the value of targeting the UPS in cancer therapy. Richardson et al., N Engl J Med, 348(26), 2609-2617 (2003). Moreover, the proteasome inhibitor bortezomib (BTZ) was shown to improve outcome in the setting of high risk cytogenetic findings. Avet-Loiseau et al., J Clin Oncol, 28(30):4630-4634 (2010); Neben et al., Blood, 119(4):940-948 (2012). Recent findings suggest that the other main class of "novel drugs", IMiDs™ also exploits the UPS, but in an opposite and less broad fashion. By increasing the affinity of the substrate recognition domain of the cereblon/CRL4 E3 ligase for Ikaros transcription factors, lenalidomide and related drugs lead to their degradation. Since these transcription factors activate production of the MM survival factor IRF4 in MM and repress IL2 transcription in T cells, their proteasomal degradation results in anti-MM and immune-stimulatory effects. Kronke et al., Science, 343(6168), 301-305 (2014). Evidence from clinical trials suggests that high cereblon expression may be required for full response and survival benefit from IMiDs™, supporting on the one hand a strategy aimed at increasing protein degradation but on the other hand revealing limitations of distal targets.

MM is characterized by transformation at or after activation of the plasma cell program in B-cells which not only maintains production of diagnostic antibodies but also entails broad survival promoting effects of its main initiator, IRF4, which is augmented in expression through a "vicious" positive feedback loop with c-MYC, and supported in survival signaling by constitutive B-cell receptor independent NF-κB activation. Furthermore, in almost half of MM patients translocation of an oncogene into the proximity of the IGH enhancer provides another link to the plasma cell program. While each of these survival proteins lend themselves to direct or indirect targeting, one way to reach them all and thereby limit adaptive escape mechanisms is by interfering with the very feature that sets MM apart from other cells: Excessive protein synthesis required for antibody production and for rapid re-supply of critical proteins with high turn-over like c-MYC.

Protein disulfide isomerase (PDI) is responsible for post-translational folding of newly synthesized proteins through reductase, oxidase, isomerase, and chaperone functions it exerts in the endoplasmic reticulum. While tried in other cancers with some success the plasma cell program should make MM exquisitely sensitive to PDI inhibition but so far this has not been attempted and testing in other cancers, thrombotic and neurodegenerative disease has so far not yielded PDI inhibitors that entered the clinic.

High risk MM affects about 20% of MM patients and reduces their life expectancy to 2-3 years. It can be classified according to clinical findings or genetic aberrations in MM cells. Although the impact of most mutations found in MM by whole genome or exome sequencing is incompletely understood, specific mutations like del 17p13, translocation 14;16, or gene expression profiles that correlate with chromosome 1 abnormalities generally predict more strongly for worse outcome than clinical factors. Other MM specific characteristics, like the number of sub-clones at diagnosis or their genomic instability increase plasticity of the neoplastic process and are probably even more important determinants of poor prognosis. Fonseca R, Monge J., Semin Oncol, 40(5), 554-566 (2013). Activation of multiple survival programs in one clone, switch between clones, and intraclonal development of new survival strategies probably converge in the highest risk myelomas.

Despite progress in the treatment of multiple myeloma, it remains an incurable cancer and most patients with bortezomib refractory disease and previous treatment with IMiDs™thalidomide and/or lenalidomide experience short progression-free and overall survival of 6 and 9 months, respectively. Kumar et al., Leukemia, 26(5), 1153 (2012). Although new treatments have been approved for these patients and more agents are in development, none of them is expected to be curative and they ultimately all select for even more resistant clones with stronger survival mechanisms.

SUMMARY OF THE INVENTION

Choosing a mechanistically unbiased approach for identifying normal bone marrow sparing anti-MM compounds with favorable pharmacokinetic activities the inventors identified a small molecule effective against all MM cell lines tested. Mechanistic studies that involved target identification with an active biotinylated analog suggested it exerts most of its action via PDI inhibition and in vivo study using an established immunocompetent systemic mouse myeloma model (5TGM1-luc) confirmed tolerability and promise as a new drug and therapeutic principle to be developed in MM.

The inventors have developed an assay for multiple myeloma (MM) drug candidates that simultaneously informs about tolerability by normal bone marrow (NLBM), stability towards liver enzymes, and anti-MM activity in the context of cell barriers, bone marrow stromal support, and short, kidney-clearance-like exposure. The lead compound (CCF642) was confirmed tolerated in NLBM samples and effective ($IC_{50}$<1 μM) in all 8 MM cell lines tested where it triggered increase of protein ubiquitination, depletion of MM survival factors c-MYC, IRF4, NF-κB, and apoptosis with degradation of all ubiquitinated proteins. Assays with recombinant and purified proteins did not explain cellular events through inhibition of deubiquitinating or activation of ubiquitinating enzymes; instead CCF642 causes protein ubiquitination and degradation by inhibiting the main enzyme responsible for post-translational folding in the ER: Protein disulfide isomerase (PDI) was pulled out from MM cells after treatment with an active biotinylated analog which was synthesized by the inventors. In vitro CCF642 inhibits PDI function and oligomerization of IRE1-α in vivo confirms accumulation of misfolded proteins in the ER. In C57BL/KaLwRij mice systemically engrafted with 5TGM1-luc CCF642 was well tolerated and about as effective against MM as bortezomib suggesting the plasma cell program not only addicts MM to the proteasome but also to post-translational folding by PDI.

In light of this work, the present invention provides protein disulfide isomerase inhibitors according formula I

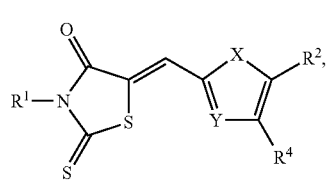

wherein $R^1$ is an aryl or cycloalkyl group, $R^2$ is selected from the group consisting of CN, $SO_2CH_3$, $NO_2$, $CO_2R^3$, $CONHR^3$, $NMe_2$, and $CF_3$, $R^3$ is selected from H or lower alkyl, $R^4$ is H, halogen, CN, or COOH, X is O or S and Y is C—H or N. The protein disulfide isomerase inhibitors can be used in a method of treatment of cancer in a subject.

BRIEF DESCRIPTION OF THE FIGURES

FIGS. 3 (A-B) provide a graph and images showing the activity of CCF642 in a syngeneic myeloma mouse model. C57BL/KaLwRij mice were injected with syngeneic 5TGM1 firefly luciferase expressing mouse myeloma cells by tail vein injection. The next day treatment was started. CCF642 was administered IP in DMSO at 25 mg/kg three times a week, controls and BTZ groups received equal amounts of DMSO. BTZ was administered at the MTD for this strain, SC twice a week at 0.5 mg/kg. FIG. 3(A) Representative life image at day 26 of the first experiment. FIG. 3(B) Survival/time (days) to euthanasia according to IACUC protocol of all mice of the first experiment (groups of 4 mice) and of a second confirmatory experiment (groups of 8 mice).

FIGS. 4(A-B) provide immunoblots showing the effect of protein ubiquitination after CCF642 administration; FIG. 4(A) Rapid increase of protein ubiquitination in three different MM cell lines after CCF642 treatment within 30 minutes is associated with PARP cleavage and subsequent decrease of protein ubiquitination suggesting protein degradation. FIG. 4(B) Selective induction of a protein degradation catastrophe in myeloma cells Immunoblots of NL BM, KG-1 myeloid leukemia, or MM1.S myeloma cells treated with CCF642 show increase in protein ubiquitination within 30 min in all cells but in NL BM and KG-1 ubiquitination is less pronounced and returns to baseline at 18 h while MM1.S cells have digested all their ubiquitinated proteins, UBA1, and the nuclear encoded cytochrome oxidase subunit cox IV at that time point. With equal protein loading, PARP, UBA1, and UBE2D1 were not detectable in normal bone marrow. The E2 conjugating enzymes UBE2D1 was included in this immunoblot to illustrate differences in baseline activity of the ubiquitin proteasome system (UPS) in the three analyzed cell types. NLBM, as expected have low (undetectable) UBE2D1 expression due to low UPS activity while UPS addicted myeloma cells express UBE2D1 strongly due to highest protein turnover among the three analyzed cell types.

FIGS. 5(A-D) provide structure, function, and binding characteristics of the biotinylated CCF642 analog.

DETAILED DESCRIPTION OF THE INVENTION

Figure 1:
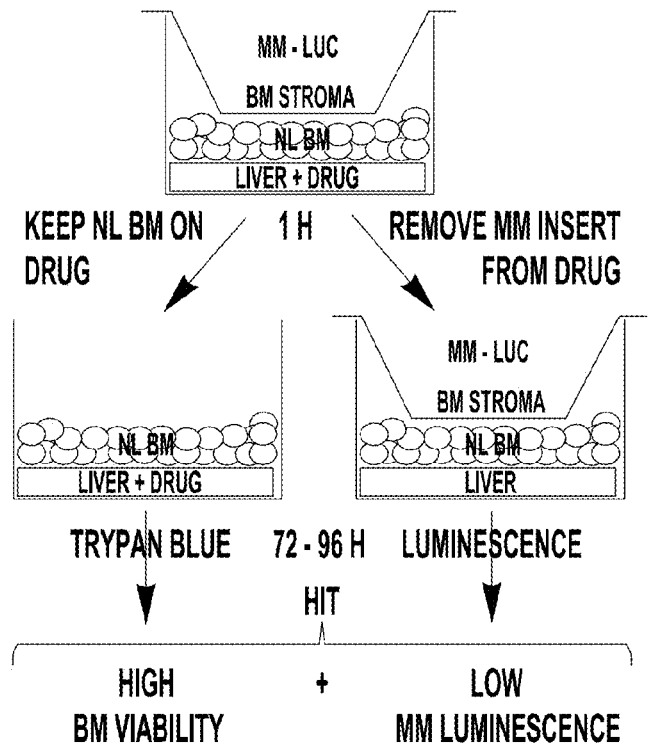
FIG. 1 provides a scheme showing a sandwich three organ system assay. HS-5 bone marrow stromal cells which secrete hematopoietic growth factors including multiple myeloma (MM) supporting IL-6 are grown to confluence on Transwell™ inserts before firefly luciferase expressing MM cells (MM-luc) are added and incubated overnight. The next day drug candidate is mixed with liver homogenate in separate plates and incubated for 30 min at 37° C. before low melting liquid agarose (cooled to 35-40° C.) is added and solidified at room temperature. Now, media and normal bone marrow (NL BM) cells, obtained from discarded bags of healthy bone marrow donors and freshly thawed, are added and HS-5/MM cell containing inserts are placed on top for 1 h (+/− as desired), then placed into drug free wells simulating kidney clearance. Three to four days later MM luciferase activity is measured and viability of NL BM, constantly drug exposed for maximal stringency, is assessed by trypan blue exclusion using Vicell™ flow.

The present invention provides protein disulfide isomerase inhibitors according to formula I

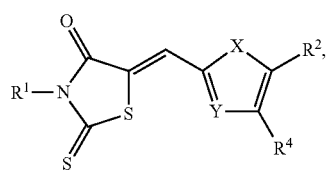

wherein $R^1$ is an aryl or cycloalkyl group, $R^2$ is selected from the group consisting of CN, $SO_2CH_3$, $NO_2$, $CO_2R^3$, $CONHR^3$, $NMe_2$, and $CF_3$ at the other end, wherein $R^3$ is selected from H or lower alkyl, $R^4$ is H, halogen, CN, or COOH, X is O or S and Y is C—H or N. The protein disulfide isomerase inhibitors can be used for treatment of cancer in a subject.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for protein disulfide isomerase inhibitors are those that do not interfere with the compounds anticancer activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A heterocyclyl group means a mono- or bicyclic ring system in which one or more carbon atoms can be replaced by one or more heteroatoms such as, for example, 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—$NR_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment also includes partial or total destruction of the undesirable proliferating cells with minimal destructive effects on normal cells. In accordance with the present invention, desired mechanisms of treatment at the cellular include, but are not limited to one or more of apoptosis, cell cycle arrest, cellular differentiation, or DNA synthesis arrest.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those having an enhanced risk of developing precancers and cancers. An elevated risk represents an above-average risk that a subject will develop cancer, which can be determined, for example, through family history or the detection of genes causing a predisposition to developing cancer.

"Pharmaceutically acceptable" as used herein means that the compound or composition is suitable for administration to a subject to achieve the treatments described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as the inhibition of protein disulfide isomerase by a detectable amount.

The term "subject" for purposes of treatment includes any human or animal subject who has a disorder characterized by unwanted, rapid cell proliferation. Such disorders include, but are not limited to cancers and precancers. For methods of prevention the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

Protein Disulfide Isomerase Inhibitors

Protein disulfide isomerase inhibitors, as defined herein, include the compounds of formula I:

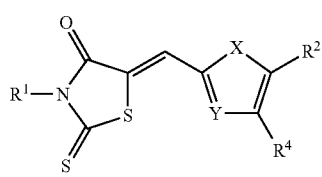

(I)

Formula 1 provides a core structure to which is attached an $R^1$ aryl or cycloalkyl group at one end and an $R^2$ is selected from the group consisting of CN, $SO_2CH_3$, $NO_2$, $CO_2R^3$, $CONHR^3$, $NMe_2$, and $CF_3$ at the other end, wherein $R^3$ is selected from H or lower alkyl, and wherein $R^4$ is H, halogen, CN, or COOH group. The heterofuryl ring of the core structure includes possible heteroatoms X and Y, wherein X is O or S and Y is C—H or N or a pharmaceutically acceptable salt thereof.

In some embodiments, $R^1$ of the compound of formula I is a substituted phenyl group. For example, in some embodiments $R^1$ has a structure according to formula II:

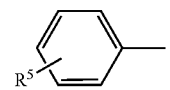

(II)

wherein $R^5$ is selected from the group consisting of —OMe, biotin, PEG,

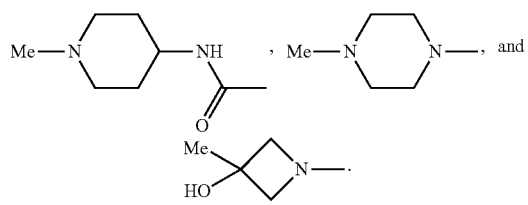

In some embodiments, $R^2$ is $NO_2$. Structure-activity studies described herein have shown that protein disulfide isomerase inhibitors according to formula I in which $R^2$ is $NO_2$ exhibit higher activity. In further embodiments, X is S and Y is methylene, thereby providing a thiophene ring.

In further embodiments, the protein disulfide isomerase inhibitor has a structure according to formula III:

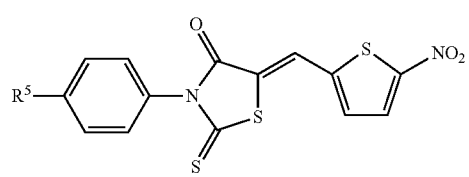

(III)

wherein $R^5$ is selected from the group consisting of —OMe, biotin, PEG,

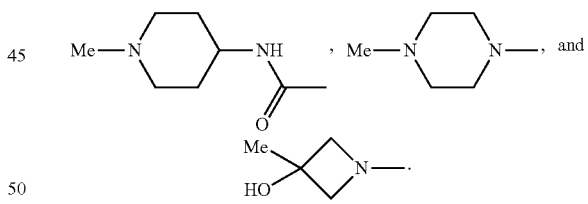

A preferred substituent at $R^5$ is a methoxy moiety (i.e., —OMe). All of the embodiments also encompass pharmaceutically acceptable salts of the indicated compounds.

A variety of additional protein disulfide isomerase inhibitors have been prepared, as shown in table I and the associated chemical structures provided below.

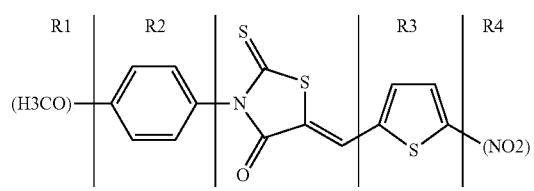

TABLE I

CCF642 derivatives

|  | R1 | R2 | R3 | R4 | PDI IC50 (μM) | PDI Activity at 10 μM (%) | MM1.S IC50 (μM) | MM1.S Viable cells at 6.75 μM (%) |
|---|---|---|---|---|---|---|---|---|
| 642-Parent | Same | Same | Same | Same | 2.44 | 21.51 | 0.25 | 8.06 |
| 642-Biotin | O—$CH_2$—NH—($C_{10}H_{16}N_2O_2S$) | Same | Same | Same | 3.14 | 29.01 | 2.86 | 15.59 |
| 642-Peg | O—($CH_2$—$CH_2$—O)$_3$—$OCH_3$ | Same | Same | Same | NR | 51.97 | 1.09 | 6.84 |
| 642-19 | None | H | Same | Same | 5.02 | 29.59 | NR | 67.62 |
| 642-20 | Same | Same | Same | $CF_3$ | NR | 72.37 | NR | 92.89 |
| 642-21 | Same | Same | Same | COOH | NR | 71.54 | NR | 101.52 |
| 642-22 | None | ($CH_2$—$CH_2$—O)$_3$—$CH_3$ | Same | Same | 6.62 | 23.33 | 1.13 | 12.63 |
| 642-23 | CN | Same | Same | Same | 1.90 | 5.92 | 0.61 | 17.48 |
| 642-24 | Same | Same | $C_6H_5$* | Same | 8.66 | 42.12 | NR | 93.46 |
| 642-25 | Same | Same | $C_6H_6O$** | $C_3H_3$ | 3.07 | 40.37 | NR | 92.82 |
| 642-26 | Same | Same | Same | $C_4H_4SBr$*** | 2.89 | 24.44 | 0.45 | 19.43 |

642-24

*::

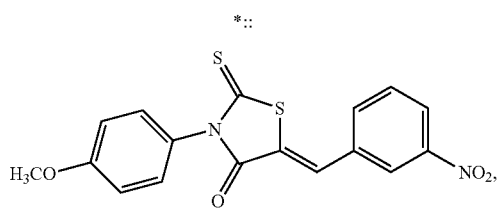

642-25

**:

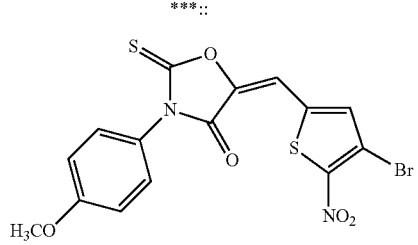

642-26

***::

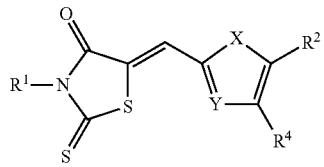

Treatment of Cancer using Protein Disulfide Isomerase Inhibitors

The present invention provides methods for treating or preventing cancer in a subject using protein disulfide isomerase inhibitors. A method of treating or cancer in a subject in need thereof by administering a therapeutically effective amount of pharmaceutically acceptable formulation comprising a compound of Formula I:

(I)

Formula 1 provides a core structure to which is attached an $R^1$ aryl or cycloalkyl group at one end and an $R^2$ is selected from the group consisting of CN, $SO_2CH_3$, $NO_2$, $CO_2R^3$, $CONHR^3$, $NMe_2$, and $CF_3$ at the other end, wherein $R^3$ is selected from H or lower alkyl, and $R^4$ is H, halogen, CN, or COOH. The heterofuryl ring of the core structure includes possible heteroatoms X and Y, wherein X is O or S and Y is C—H or N, or a pharmaceutically acceptable salt thereof. The method also encompasses embodiments including the use of any of the subsets of protein disulfide isomerase inhibitors described herein.

Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of leukemia, non-small cell lung cancer, colon cancer, central nervous system cancer, melanoma, ovarian cancer, renal cancer, prostate cancer, and breast cancer. In some embodiments, the cancer is myeloma or lymphoma.

Cancer can be treated or prevented by regulating signaling pathways within the cancerous or potentially cancerous cells to prevent excessive growth or provide regulation of other aberrant processes within the cells. While not intending to be bound by theory, the compounds of the present invention can treat or prevent cancer by causing protein ubiquitination and degradation by inhibiting the main enzyme responsible for post-translational folding in the endoplasmic reticulum; protein disulfide isomerase. Protein disulfide isomerase is known to play a role in a wide variety of different types of cancer, and therefore its inhibition can be expected to treat a wide variety of different types of cancer. Xu et al, Drug Discovery Today, 19(3):222-240 (2014). Accordingly, one aspect of the present invention provides a method of increasing ubiquitination in a cell by contacting the cell with a compound of formula I or a pharmaceutically acceptable salt thereof. The cell can be contacted in vivo, in vitro, or ex vivo. In some embodiments, the contacted cell can be a cancer cell.

Accumulation of misfolded proteins characterizes a number of diseases other than cancer. For example, misfolded protein accumulation occurs in neurodegenerative diseases such as Alzheimer's disease, and also occurs in cardiac disorders. Accordingly, some embodiments of the invention are directed to the use of protein disulfide isomerase inhibitors to treat diseases involving excessive accumulation of misfolded proteins.

Treatment, as used herein, encompasses both prophylactic and therapeutic treatment. The protein disulfide isomerase inhibitors of the invention can, for example, be administered prophylactically to a mammal prior to the development of cancer. Prophylactic administration, also referred to as prevention, is effective to decrease the likelihood that cancer will develop in the subject. Alternatively, protein disulfide isomerase inhibitors of the invention can, for example, be administered therapeutically to a subject that already has cancer. In one embodiment of therapeutic administration, administration of the protein disulfide isomerase inhibitors is effective to eliminate the cancer; in another embodiment, administration of the protein disulfide isomerase inhibitors is effective to decrease the symptoms or spread of the cancer.

The effectiveness of cancer treatment may be measured by evaluating a reduction in tumor load or decrease in tumor growth in a subject in response to the administration of the ubiquitin-activating agent. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Administration and Formulation of Protein Disulfide Isomerase Inhibitors

The present invention also provides pharmaceutical compositions that include protein disulfide isomerase inhibitors according to formula I as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The protein disulfide isomerase inhibitors can be administered as pharmaceutically acceptable salts. Pharmaceutically acceptable salt refers to the relatively non-toxic, inorganic and organic acid addition salts of the protein disulfide isomerase inhibitors. These salts can be prepared in situ during the final isolation and purification of the protein disulfide isomerase inhibitor, or by separately reacting a purified protein disulfide isomerase inhibitor with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions includes one or more protein disulfide isomerase inhibitors together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, albumin, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The protein disulfide isomerase inhibitors can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the celecoxib derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of protein disulfide isomerase inhibitor (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Reaction schemes for the preparation of various CCF-642 derivatives are shown below: Synthesis of New 4-substituted Nitro Thiophene or Furan CCF642 Derivatives

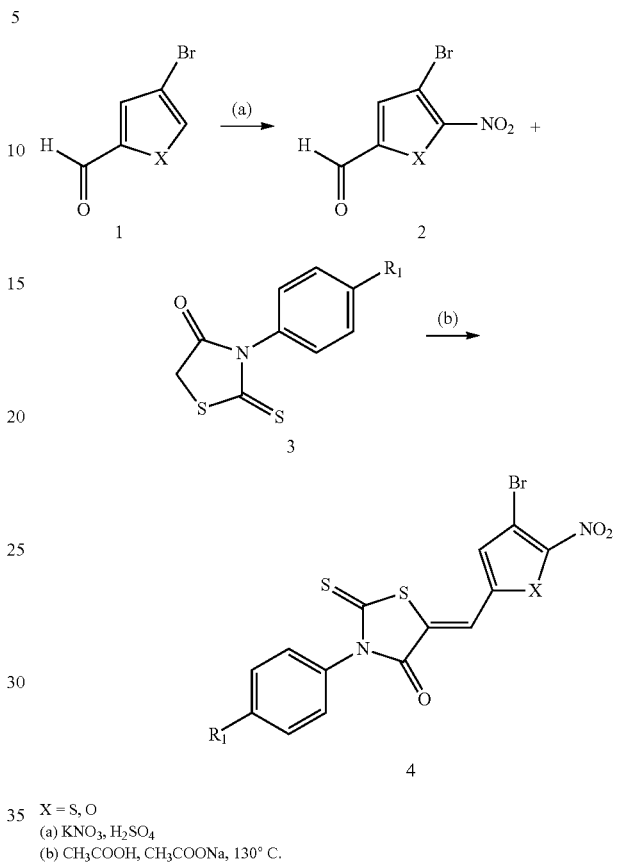

X = S, O
(a) $KNO_3$, $H_2SO_4$
(b) $CH_3COOH$, $CH_3COONa$, 130° C.

Key intermediate 2 for making libraries of new CCF642 derivatives can be modified by Suzuki, Sonagashira, Heck Coupling Reactions, as well as cyanation reactions.

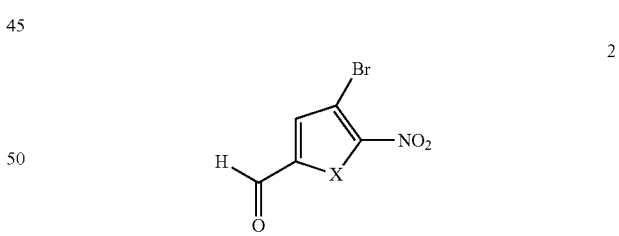

For example: Cyanation with Pd catalyst and Ferricyanide provides 4-cyano derivative 5 which can be converted as above to give 6

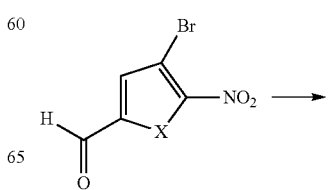

15
-continued
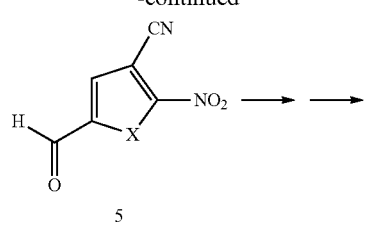
5
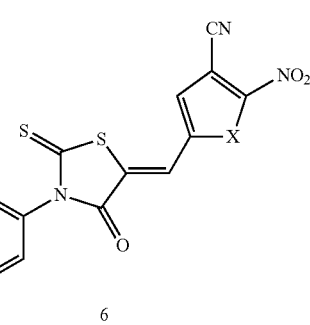
6
Suzuki Coupling Example:
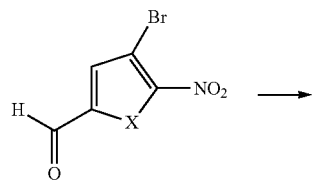
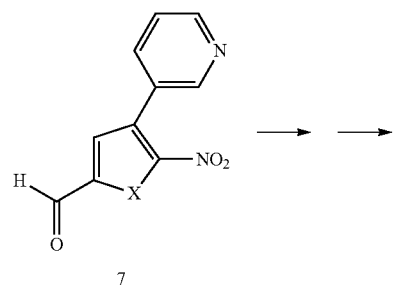
7
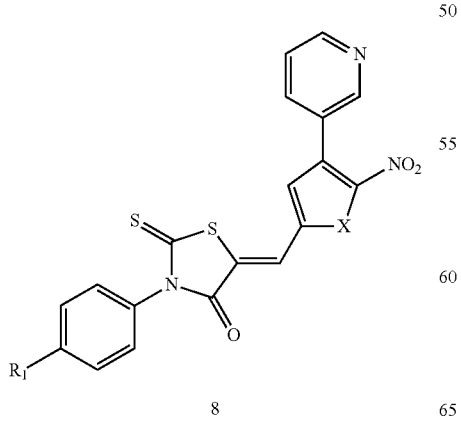
8
16
Scheme for synthesis of PEG analogs of CCF642
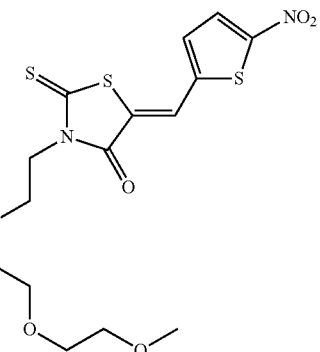
This PEG derivative shows activity and its pharmacology and drug properties can be modified by different PEG lengths and terminal functional groups
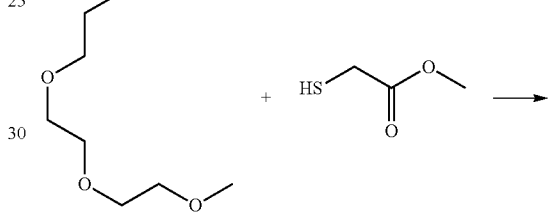
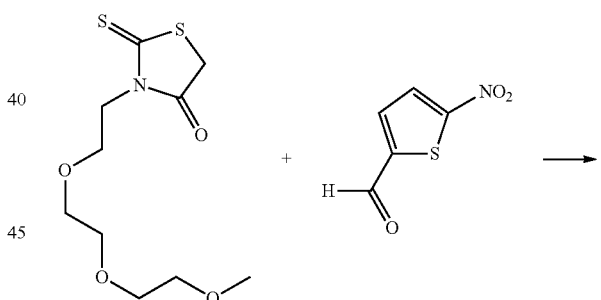
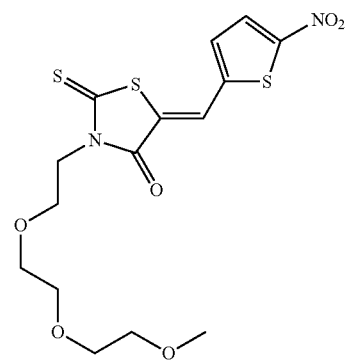 [SMILES: COCCOCCOCCN1C(=O)/C(=C/c2ccc([N+](=O)[O-])s2)SC1=S]

Other PEG derivatives can be made by starting with modified PEGS such as

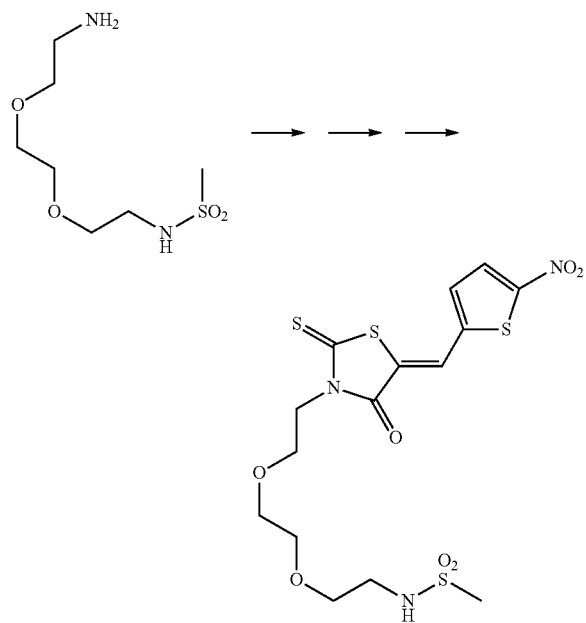

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Initial Discovery and Evaluation of CCF642

Figure 2A:
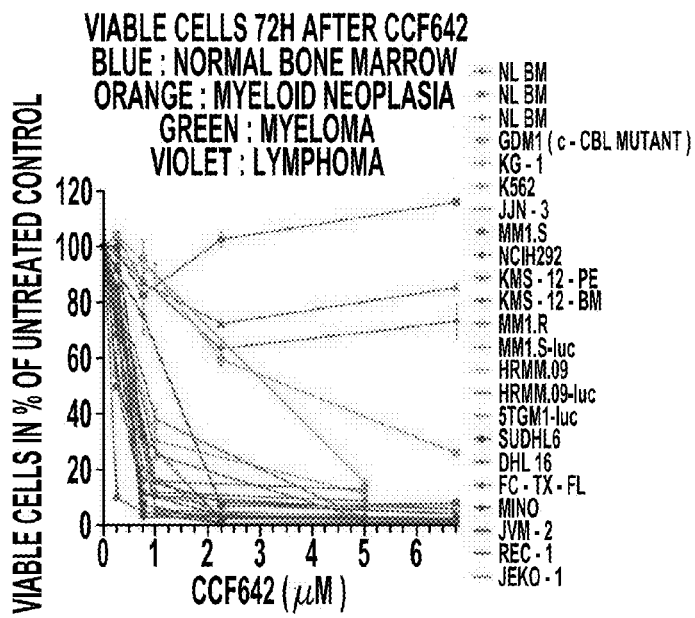
FIGS. 2(A-B) provide a graph and immunoblot showing the effect of CCF642 on cancer and protein ubiquitination, with FIG. 2(A) showing the activity of CCF642 against a panel of MM and lymphoma cells. Seventy two hours after CCF642 administration, the $IC_{50}$ by trypan blue exclusion (Vicell™) is <1 μM for all MM and all but one lymphoma line. Normal bone marrow (NL BM) tolerated CCF642; myeloid cells were less sensitive, especially GDM1, with E3 ligase domain mutation of c-CBL and FIG. 2(B) showing that an increase in protein ubiquitination is accompanied by loss of myeloma survival factors in MM cells Immunoblots of MM1.S cells show rise followed by decrease of protein ubiquitination with loss of MM survival factors.
Figure 2B:
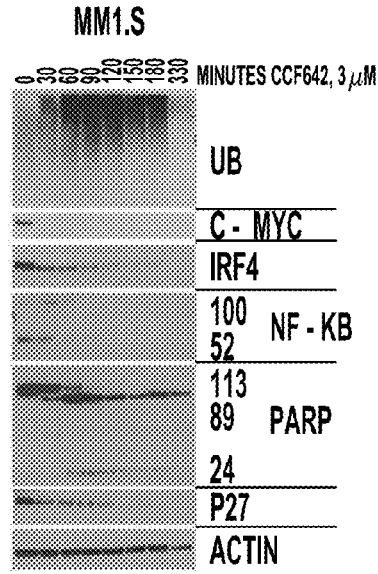
Figure 5A:
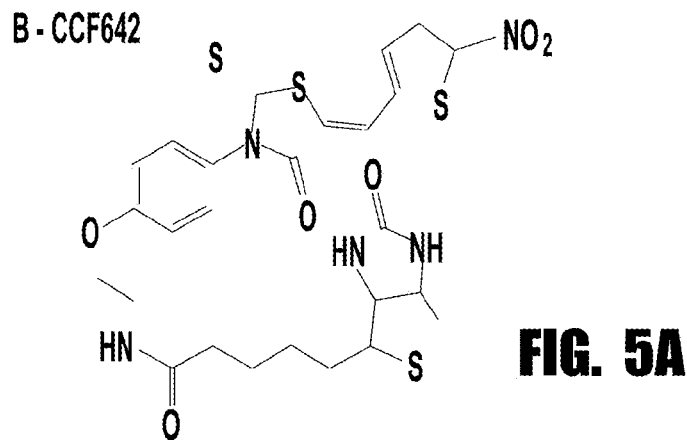
FIG. 5(A) Structure of biotinylated CCF642.(Biot-CCF642=B-CCF642)
Figure 5B:
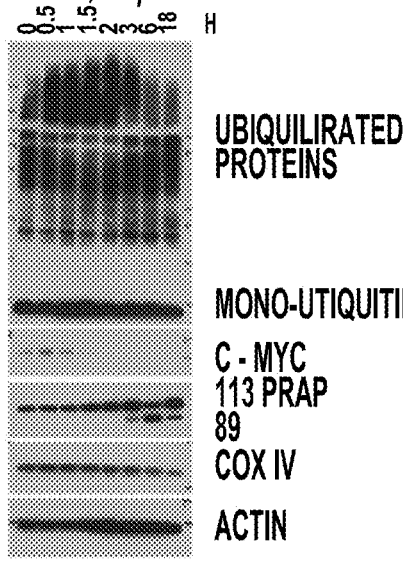
FIG. 5(B) Immunoblot of MM1.S cells treated with biotinylated CCF642 reveals similar increase in protein ubiquitination and degradation of myeloma survival factor c-MYC, PARP cleavage, and cox IV degradation as with parent compound.
Figure 5C:
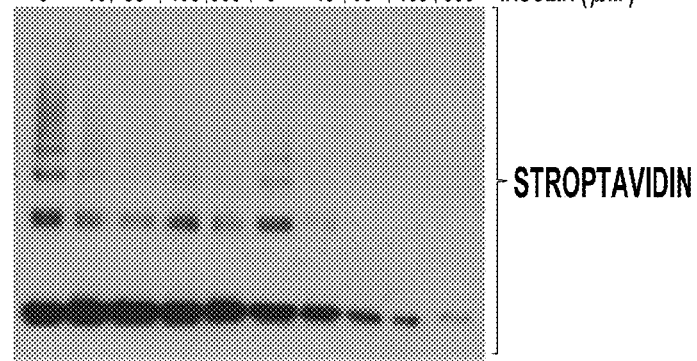
FIG. 5(C) Biotinylated CCF642 competes with the PDI substrate insulin for PDI binding. Recombinant PDI was incubated either with B-CCF642, then with insulin, or vice versa, followed by SDS-PAGE and visualization of biotin signal by horseradish peroxidase labeled streptavidin.
Figure 5D:
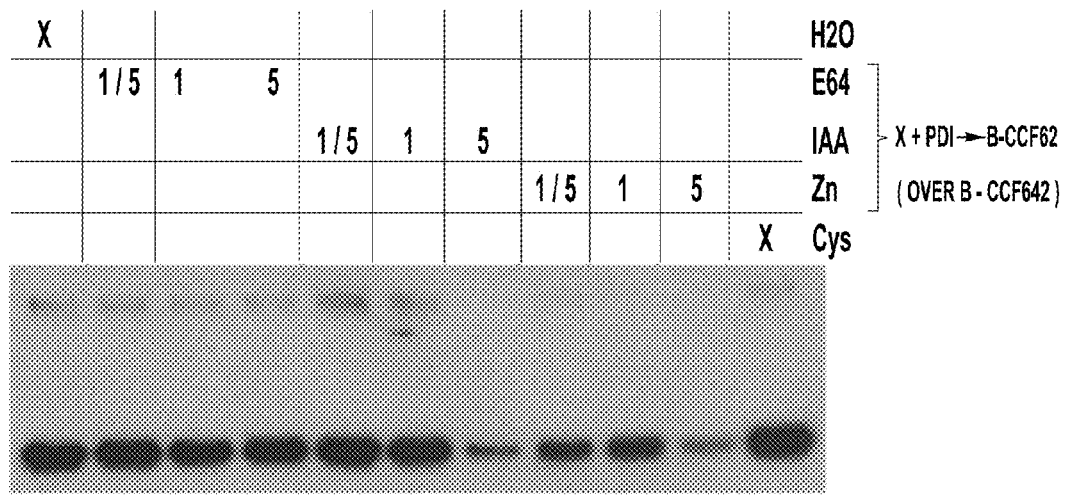
FIG. 5(D) The binding of B-CCF642 to PDI can be inhibited by cysteine reactive compounds. PDI was first incubated for 10 min with iodoacetic acid (IAA) or zinc at concentrations one fifth to five times the molar concentration of subsequently added B-CCF642, then incubated another 10 min before SDS-PAGE and biotin signal visualization. Water, the cysteine protease specific inhibitor E64, and cysteine alone were used as negative controls. IAA and zinc inhibited B-CCF642 binding suggesting it may bind to the active site cysteine of PDI.

Taking a mechanistically unbiased approach to drug discovery the inventors developed a sandwich assay that selected anti-MM compounds from a primary ATP-based screen for lack of toxicity on normal bone marrow, stability towards liver enzymes, and activity in the context of cell barriers, bone marrow stromal support, and short, kidney-clearance-like exposure (FIG. 1). CCF642 emerged as the most promising compound and in screening immunoblots after overnight incubation of MM1.S myeloma cells appeared interesting to pursue since in contrast to BTZ it depleted ubiquitinated proteins but within the few hours ubiquitination increased and c-MYC, IRF4, and NF-κB components disappeared (FIG. 2B). In all MM cell lines tested, the $IC_{50}$ for CCF642 was below 1 μM (~0.5 μM) but not reached with doses up to 6.75 μM in three independent normal bone marrow samples (FIG. 2A). After the in vivo activity was observed in a systemic syngeneic mouse MM model with response (measured by life imaging of luciferase activity) and survival comparable to BTZ (FIGS. 3A,B) the inventors investigated the mechanism of CCF642 in more detail.

Example 2

A Novel Three Organ System In Vitro Assay Identifies New Protein Disulfide Isomerase Inhibitor with In Vivo Activity Against Myeloma Methods:

Cell lines: Multiple myeloma cell lines MM1.S, MM1.R, NCI-H929 were obtained from ATCC. MM cell lines KMS-12-PE and KMS-12-BM were from the JCRB, JJN-3 from DSMZ, and 5TGM1-luc cells were from Dr. Yoneda at the University of Texas Health Science at San Antonio. HRMM.09 cells were generated in the inventor's lab from a patient who developed refractory myeloma after treatment with steroids, IMiD, proteasome inhibitors, DNA alkylators, and anthracyclines. MM1.S-luc and HRMM.09-luc were generated in the inventor's laboratory by transduction with Cignal™ firefly luciferase control lentivirus obtained from Qiagen™. Lymphoma cells were generated by Mitchell Smith. All MM and lymphoma cells were grown in RPMI 1640 (NaCl 103.45 mM, $NaCO_3$ 23.81 mM, $Na_2HPO_4$ 5.63 mM, KCl 5.33 mM, $Ca(NO_3)_2$ $4H_2O$ 0.424 mM, MgSO4 0.407 mM, pH around 7.2), supplemented with 10% fetal bovine serum, penicillin G (50 units $ml^{-1}$), and streptomycin (50 μM $ml^{-1}$). HS-5 cells were grown in appropriate cell culture media. Normal bone marrow cells were obtained from discarded bags of bone marrow grafts from healthy donors and either kept in RPMI with 25% (v/v) HS-5 supernatant for up to 14 days for isolated cytotoxicity assays or frozen and thawed for the sandwich assay. All cells were cultured at 37° C., 5% $CO_2$ in humidified air.

Reagents: The small molecule library was obtained from SPECS, recombinant proteins were from Enzo life sciences and Biovision, di-eGSSG was from Cayman chemical. Antibodies were purchased from CellSignaling.

Sandwich assay: HS-5 bone marrow stromal cells which secrete hematopoietic growth factors including multiple myeloma (MM) supporting IL-6 are grown to confluence on Transwell™ inserts before firefly luciferase expressing MM1.S cells are added and incubated overnight. The next day drug candidate is mixed with liver homogenate in separate plates and incubated for 30 min at 37° C. before low melting liquid agarose (cooled to 35-40° C.) is added and solidified at room temperature. Now, RPMI media containing 25% HS-5 supernatant and normal bone marrow (NL BM) cells, obtained from discarded bags of healthy bone marrow donors and freshly thawed, are added and HS-5/MM1.S-luc cell containing inserts are placed on top for 1 h (+/− as desired), then placed into drug free wells simulating kidney clearance. Three to four days later MM luciferase activity is measured and viability of NL BM, constantly drug exposed for maximal stringency, is assessed by trypan blue exclusion using Vicell™ flow.

PDI activity assay: The di-eosin-di-gluthathione assay was performed essentially as described (Raturi, A. and Mutus, B Free Radical Biology & Medicine 43; 2007) with the minor modification that we used gluthathione instead of DTT as reducing agent. Briefly, recombinant PDI was incubated with CC642 or analogs in potassium-based assay buffer at 37° C. before reactions were started by addition of gluthathione and di-eosin-di-gluthathione. Release of eosin was measured every 60 seconds for 30 min using excitation/emission filters of 525 nm/545 nm, respectively.

CCF642 Discovery

Taking a mechanistically unbiased approach to drug discovery the inventors developed a sandwich assay that selected anti-MM compounds from a primary ATP-based 30,000 small molecule screen for lack of toxicity on normal bone marrow, stability towards liver enzymes, and activity in the context of cell barriers, bone marrow stromal support, and short, kidney-clearance-like exposure (FIG. 1). CCF642 emerged as one of three promising compounds and had sub-$\mu$M $IC_{50}$ potency in all 8 MM cells tested and 6 of 7 lymphoma cell lines while in NLBM increase of CCF642 by about 10x above the median $IC_{50}$ in MM and lymphoma lines did not reach $IC_{50}$ (FIG. 2). Response to CCF642 was independent of TP53 mutational status and of bortezomib sensitivity.

CCF642 Mechanism

Protein ubiquitination and depletion of c-MYC, IRF4, and NF-$\kappa$B. Initial tests were aimed at excluding proteasome inhibitors from further study and used WB for accumulation of ubiquitinated proteins after one day of therapy. This revealed absence of ubiquitinated proteins in CCF642 treated MM cells while bortezomib as expected caused increase. Encouraged by these results a time-course experiment in MM1.S myeloma cells was performed that demonstrated increase in protein ubiquitination within 30 min with peak around 2 h and subsequent decrease below baseline within 4-6 h accompanied by depletion of MM survival factors and PARP cleavage suggesting protein degradation and apoptosis. C-myc, known to possess short half-life and to be regulated by proteasomal degradation disappeared first, within 30 min. Another proteasomally regulated protein, p27, disappeared as well. Other MM cells displayed a similar ubiquitination pattern (FIG. 4a) while NLBM and less responsive KG1 myeloid cells displayed less pronounced and only transient changes in ubiquitination that did not lead to degradation of essential proteins like cox IV but in KG1 partial PARP cleavage occurred (FIG. 4b) Overall, these results indicated that CCF642 induces a protein degradation catastrophe in myeloma but not normal bone marrow that involves the ubiquitin proteasome system.

CCF642 causes protein ubiquitination by inhibition of protein disulfide isomerase. To investigate how CCF642 increased protein ubiquitination, the inventors first tested whether it would inhibit deubiquitinases. Since c-myc was the first protein to disappear, USP28, a deubiquitinase responsible for stabilizing c-myc, was used in polyubiquitin cleavage assays. CCF642 did not inhibit USP28 mediated cleavage of ubiquitin 5-7 mers (data not shown). To test whether other deubiquitinases might be inhibited, ubiquitination reactions were performed with HeLa fractions that contain all major ubiquitinating and deubiquitinating enzymes. These assays, run with and without concurrent proteasome inhibition failed to detect any increase in ubiquitination ruling out inhibition of deubiquitinases as mechanism (data not shown). To identify CCF642's target the inventors performed medicinal chemistry modifications to identify sites that could be modified without loss of activity and then attached biotin. Treatment of MM1.S cells with this biotinylated analog similarly led to protein ubiquitination and decrease in c-myc (FIG. 5) supporting its use for target identification. First, the inventors tested whether this analog would react with recombinant proteins of the ubiquitination cascade. These experiments showed that it covalently bound to the E1 ubiquitin activating enzyme UBA1 but not to 10 different E2 enzymes, or ubiquitin (data not shown). The binding to UBA1 was inhibited by cysteine alkylation with iodoacetamide and could be reversed by addition of ATP and ubiquitin, suggesting CCF642 binds at the active site cysteine. In vitro ubiquitination reactions with UBA1, ubiquitin, and E2 enzymes showed no difference in ubiquitination at 1 min to 1 h but when target proteins were included by using HeLa fractions, the inventors could see reduced protein ubiquitination at 2-4 h with use of 1 $\mu$M CCF642 (data not shown). Thus, the effects of CCF642 on UBA1 may contribute to the decrease in ubiquitination in cells but not the initial increase and massive protein degradation.

Next, MM1.S cells were treated with B-CCF642 and purified lysates of treated and untreated cells for B-CCF642 binding proteins using streptavidin beads followed by SDS-PAGE and mass spectroscopy for protein sequencing of a band that contained biotin signal. Among 10 proteins that were only recovered from treated cells PDI was the most abundant but HSP70 family members were also recovered. To test whether HSP70 family members were inhibited by CCF642, chaperone assays were performed that tested rearrangement of partially denatured luciferase. In these assays CCF642 did not inhibit reactivation of luciferase activity by HSP70 (data not shown). However, PDI function, as assessed by the eGSSG assay which measures PDI's reducing capacity, was inhibited by CCF642 (table 1). Incubation of recombinant PDI with B-CCF642 followed by SDS-PAGE revealed covalent binding that could be blocked by cysteine alkylation using iodoacetic acid (IAA) or the cysteine reactive metal Zn but cysteine itself did not inhibit binding. This suggested that CCF642 may bind to active site cysteines of PDI. To determine whether PDI activity is inhibited in vivo, the inventors performed IRE1-$\alpha$ immunoblots after CCF642 treatment of MM1.S cells. IRE1-$\alpha$ acts as a sensor for misfolded proteins in the ER and undergoes oligomerization after it binds to misfolded proteins which changes its conformation into an active state. Lavoie et al., Trends in biochemical sciences, 39(10):475-486 (2014). Within 15 min CCF642 caused IRE1-$\alpha$ oligomerization (FIG. 6) which was associated with increase in protein ubiquitination (FIGS. 2b and 4), a well-documented consequence of reduction in PDI activity. Lee et al., EMBO molecular medicine. 6(6):732-743 (2014). In conclusion mechanistic studies suggest that CCF642 increases protein ubiquitination and degradation by interfering with post translational protein folding in the ER through inhibition of PDI.

In Vivo Activity

Figure 7:
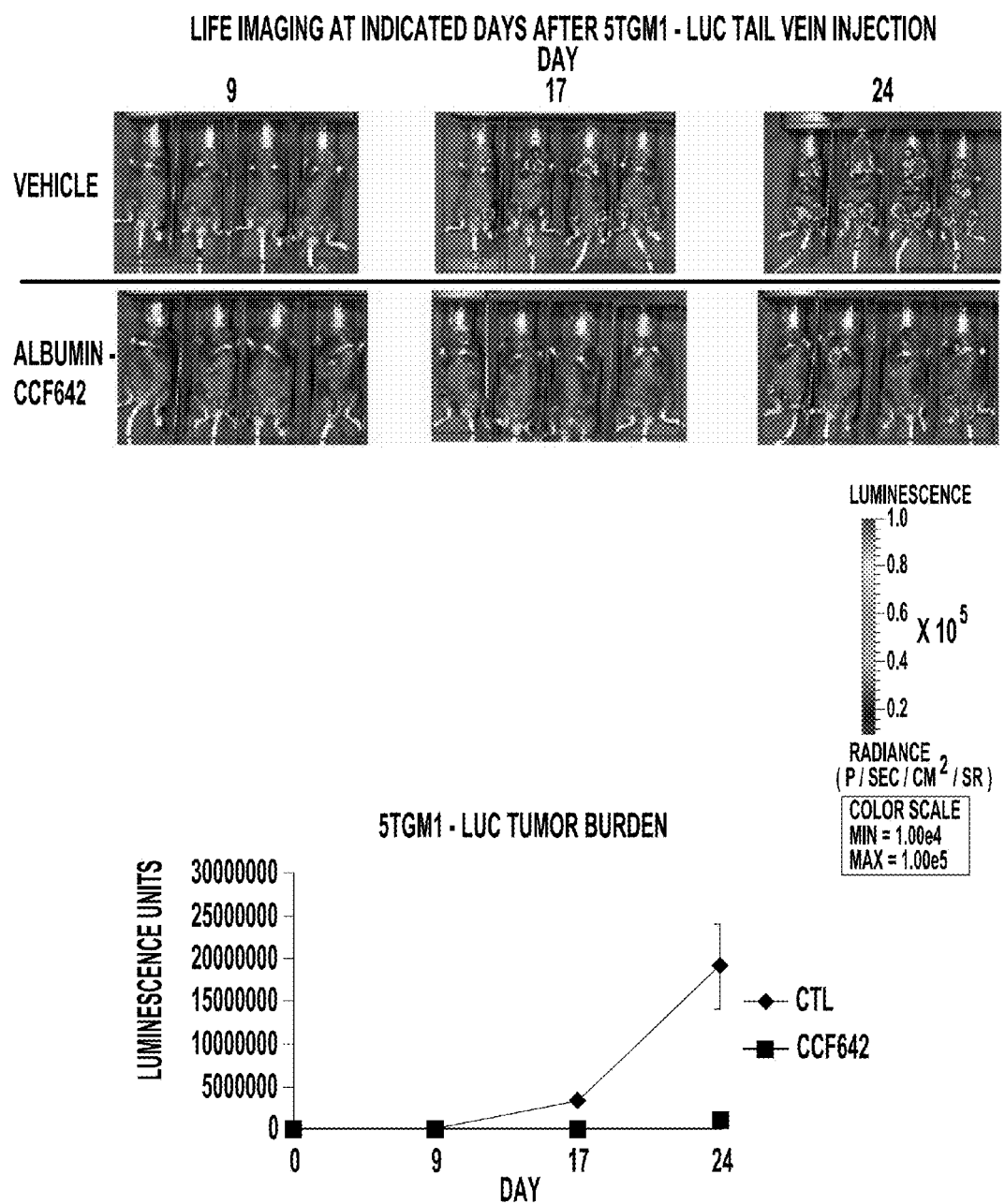
FIG. 7 provides graphs and images showing CCF642 at 7.5 mg/kg in 10-20% bovine serum albumin and <10% DMSO IP three times a week, starting one day after tail vein injection of syngeneic 5TGM1-luc myeloma cells into C57BL/KaLwRij mice, is effective in vivo. Error bars in the graph represent standard error of the mean for luminescence units. In contrast to the DMSO-based CCF642 formulation, this albumin-based formulation can be given IV to mice without any obvious side effects. It may therefore serve as model for translation into human evaluation where human albumin would be used.
Figure 8:
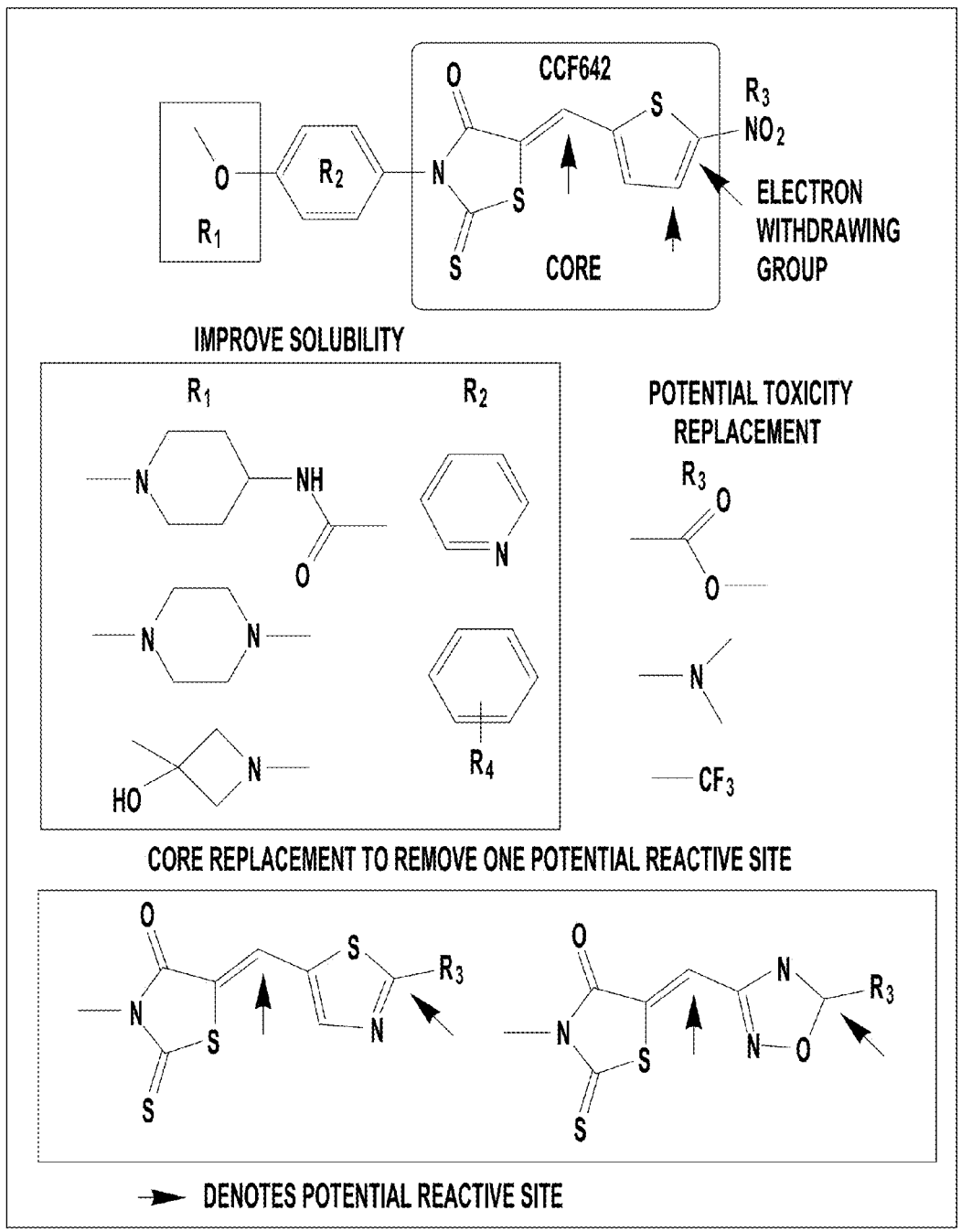
FIG. 8 provides a scheme showing the proposed chemical modifications to improve the solubility and selectivity of CCF642.

To evaluate in vivo activity of CCF642 against MM we used a syngeneic model with tail vein injection of luciferase expressing 5TGM1 cells (5TGM1-luc) into C57BL/KaL-wRij mice. Treatment with CCF642 at 25 mg/kg in DMSO IP three times a week suppressed luciferase signal gain and prolonged life of mice about as much as bortezomib 0.5 mg/kg SC twice a week, the maximal tolerated dose of bortezomib the inventors determined for this mouse strain (FIG. 3). Since DMSO-based does not stay in solution when in contact with aqueous solution the inventors changed the formulation of CCF642 and prepared it in 10-20% bovine serum albumin, isotonic saline, and 10% DMSO. This formulation retained activity against myeloma cells in vitro (data not shown) and was tolerated by mice when given IV (data not shown). Since it was expected to keep CCF642 in solution after IP injection another animal experiment was performed at a dose of 7.5 mg/kg IP three times a week which achieved similar in vivo 5TGM-1-luc suppression as 25 mg/kg of the DMSO-based formulation (FIG. 7). Discussion:

The discovery of a novel anti-myeloma drug candidate with inhibitory function on a key enzyme for post translational folding (PDI), identified from a mechanistically unbiased screen which prioritized tolerance by normal bone marrow while simulating liver and kidney to increase likelihood of in vivo activity, is described herein.

Efficacy in vivo with anti-myeloma activity as determined by in vivo imaging and survival benefit comparable to bortezomib in a syngeneic mouse myeloma model (FIG. 3) confirms that the three organ system cell-based screening system (FIG. 1) can identify promising drug candidates. CCF642 was one of three compounds from a 30,000 small molecule screening algorithm that demonstrated hit qualities in this final pre-animal test. The two other compounds are currently in the animal study stage and preliminary results suggest activity. A number of variables can be adjusted in this assay, including drug doses, cancer and bone marrow drug exposure times, making hit selection dependent on limits set by the investigator but in contrast to most other assays it allows assessment of toxicity and efficacy in the context of pharmacokinetic influences. The described setup with lymphoid and myeloid growth factor secreting HS-5 bone marrow stroma cells as niche, documented to confer resistance to myeloid and lymphoid cells, should be applicable to a variety of bone marrow cancers but would require adjustment for solid tumors, which may best be examined with stroma from their tissue of origin.

Figure 6:
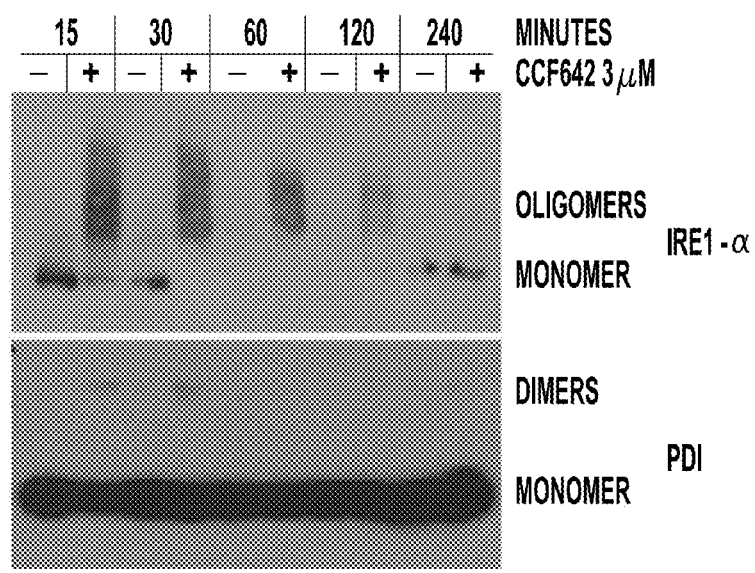
FIG. 6 shows IRE1-α oligomerization within 15 minutes after CCF642 treatment in MM1.S myeloma cells as evidence for accumulation of misfolded proteins in the endoplasmic reticulum.

Success of the proteasome inhibitor bortezomib has established protein homeostasis as a valid target for lymphoid malignancies. Bose et al., Expert Opin Pharmacother., 15(16):2443-59 (2014). This has fueled research into most other characterized components of the ubiquitin proteasome system. Zhang W, Sidhu S S., FEBS Lett., 588(2):356-367 (2014). One inhibitor of UBA1 (MLN7243) that acts on the AMP-ubiquitin binding site of UBA1 is already in clinical trial in solid tumors (NCT02045095); the proposed mode of action is induction of ER stress from upstream inhibition of proteasomal degradation that also increases half-life of c-MYC Inhibitors of protein disulfide isomerase as another way to cause ER stress by overwhelming cancer cells with misfolded proteins and interfering with supply of correctly folded survival factors are also actively pursued. Xu et al., Drug discovery today. 19(3):222-240 (2014). Since secretion of PDI from platelets and endothelial cells at sites of injury represents an early step in platelet aggregation and fibrin generation that can be suppressed in model systems by PDI inhibitors, thrombotic disease may become one of their indications. Flaumenhaft et al., "Therapeutic Implications of Protein Disulfide Isomerase Inhibition in Thrombotic Disease," Arteriosclerosis, thrombosis, and vascular biology. Aug. 7, 2014; Jasuja et al., J Clin Invest., 122(6):2104-2113 (2012). Paradoxically, neurodegenerative diseases that are characterized by production of misfolded proteins like mutant huntingtin may also benefit. Mutant huntingtin attracts PDI to mitochondrial membranes resulting in mitochondrial membrane potential destabilization and neuronal cell death which can be prevented by PDI inhibition. Hoffstrom et al., Nature chemical biology., 6(12):900-906 (2010). So far, no PDI inhibitor has entered clinical trial, maybe in part because screening mechanisms focused on biochemical tests yielding few candidates with favorable in vivo properties. The inventors approach to screen for clinically promising drug candidates and then investigate mechanism of lead compounds provided an anti-myeloma drug candidate with in vivo activity and no obvious toxicity that displayed all features expected from a PDI inhibitor: Oligomerization of IRE1-α as sign of misfolded ER proteins, ubiquitination, protein degradation, and selective induction of cell death in myeloma but not normal bone marrow cells that, due to lower protein turnover and baseline ER stress are expected to be less dependent on maximal PDI activity. Synthesis of an active biotinylated analog allowed the inventors to pull out PDI as the main cellular target protein which was inhibited by CCF642 in vitro (table 1). While no assay for direct analysis of PDI activity in cells has been reported yet, the inventors' data confirm accumulation of misfolded proteins in the ER after MM1.S treatment with CCF642 as indirect evidence for PDI inhibition (FIG. 6). Binding of CCF642 to PDI was inhibited by cysteine modification or competition suggesting it occurred via active site cysteines of the α or α' domain (two in each) cysteines in the b or b' domain. Ongoing SAR studies (table 1) yield insight into molecular features important for PDI inhibition and for reaching cellular PDI that will facilitate development of optimized analogs. For example, the soluble group frequently used in drug development will be introduced to replace the methoxy group of CCF642 which has been shown not to interfere with its potency in the biotinylated and pegylated analogs.

Mechanistic investigations revealed that in addition to binding to and inhibiting PDI, CCF642 interacted with ubiquitin activating enzyme UBA1 with covalent, cysteine dependent binding that could be reversed by ATP and ubiquitin. In vitro, this did not result in significant enhancement of ubiquitination but at higher doses or with extension of ubiquitination reactions over 1 h inhibition of UBA1 could be seen. In vivo such UBA1 inhibition could limit cellular response to accumulation of misfolded proteins but since proteins known to be regulated by proteasomal degradation like c-myc and p27 were rapidly depleted in myeloma cells treated with CCF642 (FIG. 2b), inhibition of UBA1 does not appear to contribute significantly to observed anti-myeloma efficacy of CCF642. Its scaffold may however prove useful for the development of UBA1 inhibitors.

While CCF642 may affect additional proteins its main effect on myeloma appears to be mediated via PDI inhibition with degradation of all major myeloma survival factors triggered by misfolding in the ER. Excellent tolerance and activity in mice supports further development of CCF642 and derived PDI inhibitors in myeloma.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A compound of formula I

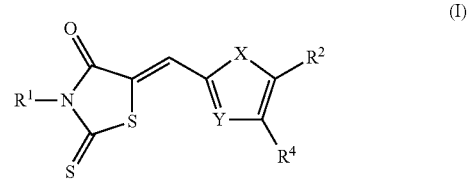

wherein:

$R^1$ has a structure according to formula II:

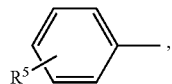
(II)

wherein $R^5$ is selected from the group consisting of biotin, PEG,

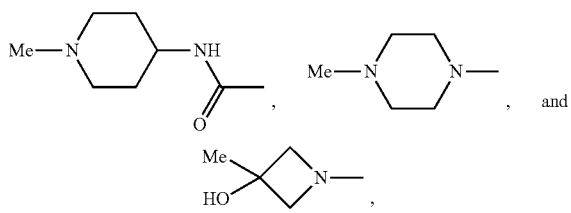
, and $R^2$ is selected from the group consisting of CN, $SO_2CH_3$, $NO_2$, $CO_2R^3$, $CONHR^3$, $NMe_2$, and $CF_3$, $R^3$ is selected from H or lower alkyl, $R^4$ is selected from H, halogen, CN, or COOH, X is O or S and Y is C—H or N, or a pharmaceutically acceptable salt thereof.

2. The compound of claim 1, wherein $R^2$ is $NO_2$.

3. The compound of claim 2, wherein $R^4$ is bromine.

4. The compound of claim 1, wherein X is S and Y is —CH=.

5. The compound of claim 1, wherein the compound has a structure according to formula III:

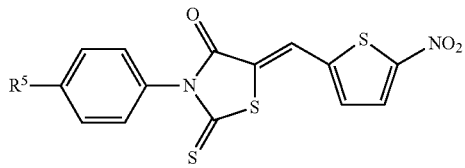
(III)

wherein $R^5$ is selected from the group consisting of biotin, PEG,

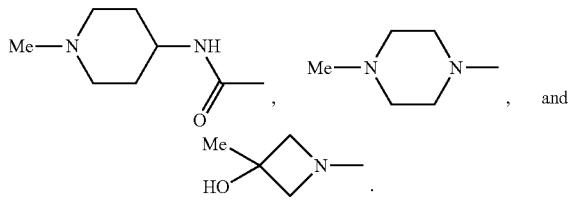
, and

6. A method of therapeutic treatment of myeloma or lymphoma in a subject in need thereof by administering a therapeutically effective amount of pharmaceutically acceptable formulation comprising a compound of Formula I:

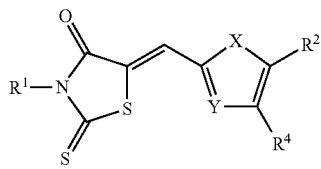
(I)

wherein:

$R^1$ is an aryl or cycloalkyl group, $R^2$ is selected from the group consisting of CN, $SO_2CH_3$, $NO_2$, $CO_2R^3$, $CONHR^3$, $NMe_2$, and $CF_3$, $R^3$ is selected from H or lower alkyl;

$R^4$ is selected from H, halogen, CN, or COOH;

X is O or S and Y is C—H or N, or a pharmaceutically acceptable salt thereof, to the subject.

7. The method of claim 6, wherein $R^1$ is a substituted phenyl group.

8. The method of claim 7, wherein $R^1$ has a structure according to formula II:

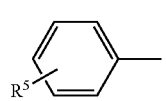
(II)

wherein $R^5$ is selected from the group consisting of —OMe, biotin, PEG,

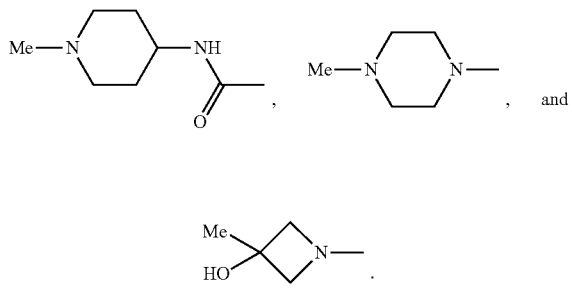
, and

9. The method of claim 6, wherein $R^2$ is $NO_2$.

10. The method of claim 9, wherein $R^4$ is bromine.

11. The method of claim 6, wherein X is S and Y is —CH=.

12. The method of claim 6, wherein the compound has a structure according to formula III:

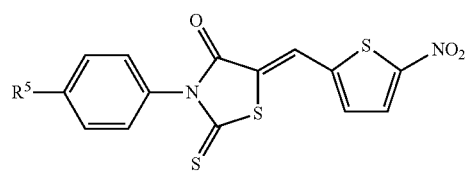
(III)

wherein $R^5$ is selected from the group consisting of —OMe, biotin, PEG,
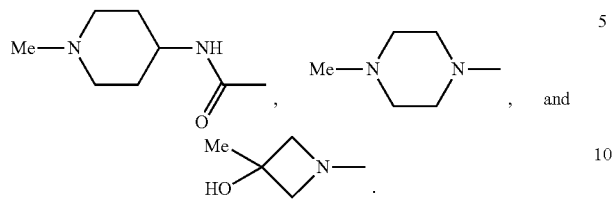
13. The method of claim 12, wherein $R^5$ is —OMe.
14. The method of claim 6, wherein the subject is human.